United States Patent [19]
Eastman

[11] Patent Number: 5,284,993
[45] Date of Patent: Feb. 8, 1994

[54] ALKYLATION CATALYST REGENERATION

[75] Inventor: Alan D. Eastman, Bartlesville, Okla.

[73] Assignee: Phillips Petroleum Company, Bartlesville, Okla.

[21] Appl. No.: 947,611

[22] Filed: Sep. 21, 1992

[51] Int. Cl.$^5$ .............................. C07C 7/04; C07C 2/62
[52] U.S. Cl. ...................................... 585/842; 502/27; 585/718; 585/719; 585/723; 585/857; 585/868
[58] Field of Search ............... 585/842, 857, 868, 723, 585/718, 719

[56] References Cited

U.S. PATENT DOCUMENTS

| | | | |
|---|---|---|---|
| 3,778,489 | 12/1973 | Parker et al. | 585/723 |
| 3,887,635 | 6/1975 | Parker et al. | 585/723 |
| 3,925,318 | 12/1975 | Parker et al. | 260/683.58 |
| 4,035,242 | 7/1977 | Brandt | 203/15 |
| 4,316,998 | 2/1982 | Van Pool | 585/842 |

Primary Examiner—Asok Pal
Attorney, Agent, or Firm—Charles W. Stewart

[57] ABSTRACT

Disclosed is a process for removing acid soluble oils, produced as an undesirable by-product of an acid catalyzed alkylation reaction, from a mixture containing a strong acid and methanesulfonic acid. The process includes the use of water to induce the formation of the two immiscible liquid phases of ASO and methanesulfonic acid with water. The two immiscible phases can subsequently be separated from each other.

24 Claims, 1 Drawing Sheet

ALKYLATION CATALYST REGENERATION

The present invention relates to the regeneration of a catalyst composition utilized in a hydrocarbon conversion process. More particularly, the invention relates to the regeneration of a catalyst mixture, comprising a strong acid component and methanesulfonic acid, utilized in the alkylation of olefin hydrocarbons by isoparaffin hydrocarbons.

BACKGROUND OF THE INVENTION

It has been discovered that a mixture, comprising a strong acid component and methanesulfonic acid, can be an effective catalyst for use in the alkylation of olefin hydrocarbons by isoparaffin hydrocarbons to produce an alkylate reaction product, or alkylate. The alkylate reaction product generally contains hydrocarbons having seven or more carbon atoms, and it is a highly desirable gasoline blending component because of its high octane value as a motor fuel.

While a process which utilizes a catalyst composition comprising a strong acid component and methanesulfonic acid produces an alkylate product of good quality, one side effect from using such a process in the production of alkylate is the formation of certain polymeric reaction by-products such as those referred to as acid-soluble oils, or ASO. These polymeric reaction by-products are referred to as acid-soluble oils because they are soluble in the catalyst utilized in the alkylation process and, thus, remain in the catalyst phase when the alkylate product resulting from the contact of a hydrocarbon mixture with an alkylation catalyst is separated from the alkylation catalyst. In an alkylation process which continuously separates the catalyst phase from the alkylation reaction product for reuse in the process reaction zone, there is a buildup of ASO in the catalyst. Over time, the ASO concentration will reach unacceptable concentration levels if not removed. A low concentration of ASO in the alkylation catalyst comprising a sulfone component and a hydrogen halide component is believed to have a beneficial effect upon the alkylation process or its product. However, higher concentrations of ASO in the alkylation catalyst have an adverse effect upon the catalyst activity and the final alkylate end-product. An ASO concentration in the alkylation catalyst that exceeds certain acceptable limits will result in lowering the octane of the alkylate end-product with incremental increases in the ASO concentration causing incremental decreases in the alkylate octane.

SUMMARY OF THE INVENTION

It is therefore an object of this invention to provide a novel process for the removal of ASO from alkylation catalysts, particularly, from mixtures comprising a strong acid and methanesulfonic acid.

Thus, the process of the present invention relates to the removal of ASO from a mixture containing a strong acid, methanesulfonic acid and ASO. The mixture is passed to a separation zone, which is maintained at such conditions as to induce the flash separation of at least a portion of the strong acid component of the mixture and to provide an acid in vapor phase stream and a liquid phase stream. The acid in vapor phase stream can comprise at least a portion of the strong acid component of the mixture, and the liquid phase stream can comprise methanesulfonic acid and ASO. Water is then mixed with the liquid phase stream to form a hydrous liquid phase stream. The amount of water mixed with the liquid phase stream is such that it is effective for causing the subsequent formation of an ASO phase and a methanesulfonic acid with water phase. The ASO phase comprises ASO and the methanesulfonic acid with water phase comprises methanesulfonic acid and water.

Figure 1:
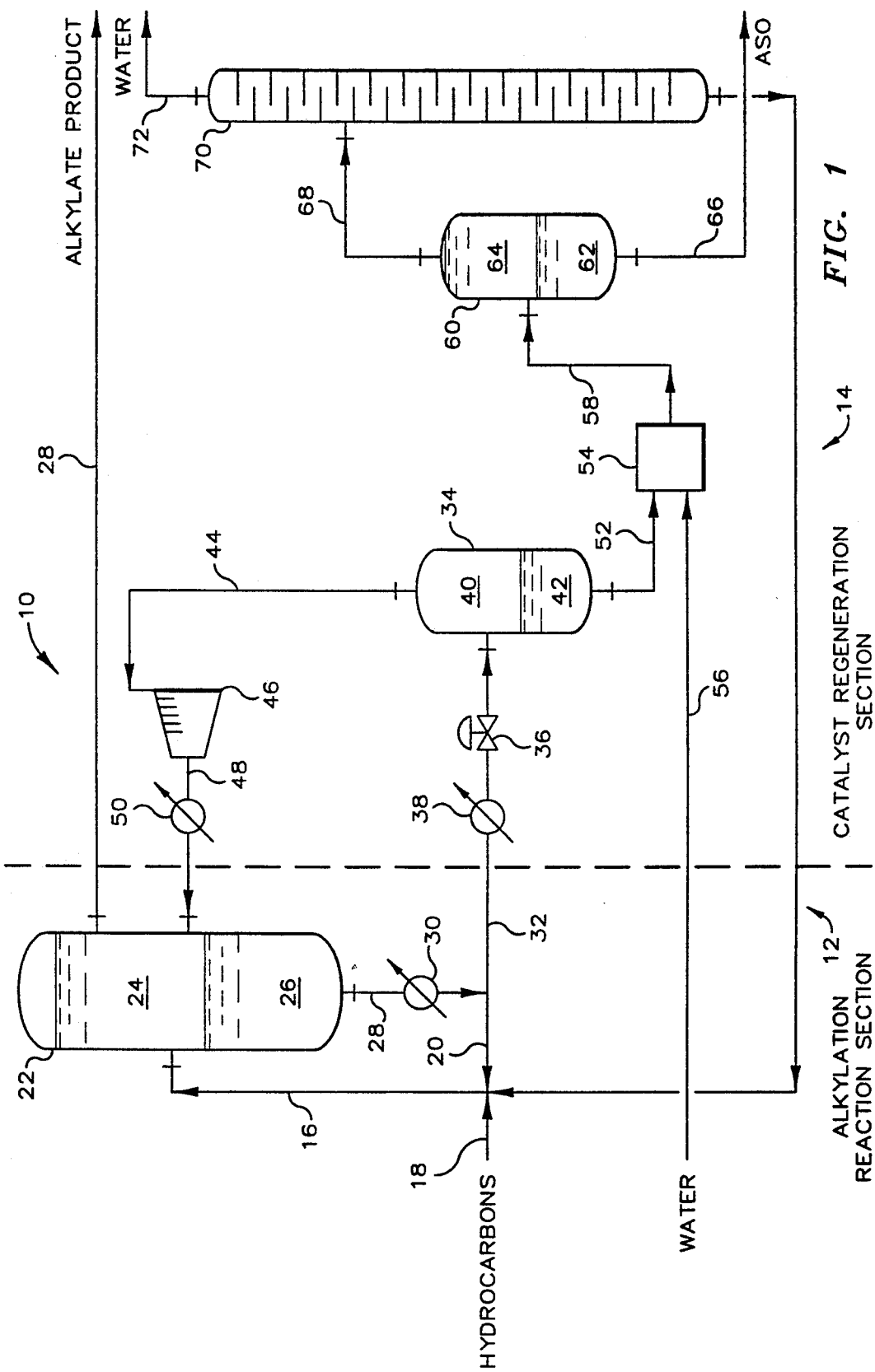
FIG. 1 provides a schematic representation of the process which is one embodiment of the invention.

Other objects and advantages of the invention will be apparent from the foregoing detailed description of the invention and the appended claims.

DETAILED DESCRIPTION OF THE INVENTION

The acid soluble oil composition referred to herein is produced as a reaction by-product in an alkylation process comprising the step of contacting a hydrocarbon mixture, which comprises olefins and isoparaffins, with an alkylation catalyst, which comprises, consists of, or consists essentially of a strong acid component and a methanesulfonic acid component. As referred to within this description and in the claims, the term "acid soluble oil", or "ASO", means those conjunct polymers which are highly olefinic oils produced by acid-catalyzed reactions of hydrocarbons. An extensive description and characterization of certain types of conjunct polymer oils is provided in the *Journal of Chemical and Engineering Data* article entitled "Molecular Structure of Conjunct Polymers", pages 150-160, Volume 8, Number 1, by Miron and Lee. This article is incorporated herein by reference. The physical properties of ASO depend upon the particular hydrocarbon feed processed, the catalyst utilized in the process, feed contaminants such as hydrogen sulfide, butadiene, oxygenates and other compounds, and the alkylation process reaction conditions. Thus, as the term is more narrowly defined herein, ASO will be those conjunct polymers produced as a by-product in the catalyzed reaction of monoolefins with isoparaffins utilizing a catalyst mixture comprising, consisting of, or consisting essentially of a strong acid component and a methanesulfonic acid component. The preferred monoolefins for use in the catalyzed reaction are those having from three to five carbon atoms and the preferred isoparaffins are those having from four to six carbon atoms. The preferred strong acid component is either halosulfuric acid or trihalomethanesulfonic acid, or both. Most preferably, the strong acid is selected from the group consisting of fluorosulfonic acid, trifluoromethanesulfonic acid, and mixtures thereof.

The ASO by-product derived from the hydrocarbon reaction catalyzed by the alkylation catalyst can further be generally characterized as having a specific gravity, with water at 60° F. as the reference, in the range of from about 0.8 to about 1.0, an average molecular weight in the range of from about 250 to about 350, and a bromine number in the range of from about 40 to about 350.

The alkylation catalyst used in the alkylation process wherein an ASO reaction by-product is produced can comprise, consist of, or consist essentially of a strong acid component such as halosulfuric acid ($XSO_3H$), trihalomethanesulfonic acid ($CX_3SO_3H$) or mixtures thereof and a methanesulfonic acid ($CH_3SO_3H$) component. Preferably, the ASO by-product will be produced in an alkylation process in which the hydrocarbon mixture is contacted with an alkylation catalyst having either fluorosulfonic acid or trifluoromethanesulfonic acid as its strong acid component.

To obtain good alkylation results, the alkylation catalyst of the present invention can comprise methanesulfonic acid and any suitable amount of strong acid that is sufficient to provide a high quality alkylate product when utilized in a process for alkylating olefin compounds with isoparaffin compounds. It is preferred, however, for the alkylation catalyst composition to be a mixture of a strong acid such as halosulfuric acid or trihalomethanesulfonic acid, or both, and methanesulfonic acid having a molar ratio of strong acid-to-methanesulfonic acid in the range of from about 0.8 to about 2.0. Preferably, the molar ratio of strong acid-to-methanesulfonic acid can range from about 1.0 to about 1.7, and, most preferably, the molar ratio of strong acid-to-methanesulfonic acid can range from 1.1 to 1.3.

The trifluoromethanesulfonic acid component of the alkylation catalyst composition has a chemical formula of $CF_3SO_3H$. Typical commercial grades of trifluoromethanesulfonic acid can be used to formulate the catalyst composition. In general, these commercial grades should have purities of at least 98 weight percent of trifluoromethanesulfonic acid.

The fluorosulfonic acid component of the alkylation catalyst composition has a chemical formula of $FSO_3H$. Typical commercial grades of fluorosulfonic acid can be used to formulate the catalyst composition. In general, these commercial grades should have purities of at least 98 weight percent of fluorosulfonic acid.

The methanesulfonic acid utilized as a component of the catalyst composition has the chemical formula of $CH_3SO_3H$. Any suitable commercial grade of methanesulfonic acid can be used to formulate the catalyst composition; but, preferably, the commercial grade of methanesulfonic acid should have a purity of at least 99 weight percent.

Alkylation processes contemplated in the present invention are those liquid phase processes wherein monoolefin hydrocarbons such as propylene, butylenes, pentylenes, hexylenes, heptylenes, octylenes and the like are alkylated by isoparaffin hydrocarbons such as isobutane, isopentane, isohexane, isoheptane, isooctane and the like for production of high octane alkylate hydrocarbons boiling in the gasoline range and which are suitable for use in gasoline motor fuel. Preferably, isobutane is selected as the isoparaffin reactant and the olefin reactant is selected from propylene, butylenes, pentylenes and mixtures thereof for production of an alkylate hydrocarbon product comprising a major portion of highly branched, high octane value aliphatic hydrocarbons having at least seven carbon atoms and less than ten carbon atoms.

In order to improve selectivity of the alkylation reaction of the present invention toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8 to 15. It is emphasized, however, that the above recited ranges for the molar ratio of isoparaffin-to-olefin are those which have been found to be commercially practical operating ranges; but, generally, the greater the isoparaffin-to-olefin ratio in an alkylation reaction, the better the resultant alkylate quality.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 120° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst of the present invention generally should be sufficient to provide for essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40-90 volume percent catalyst phase and about 60-10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

The alkylation process can be carried out either as a batch or continuous type of operation, although it is preferred for economic reasons to carry out the process continuously. It has been generally established that in alkylation processes, the more intimate the contact between the feedstock and the catalyst the better the quality of alkylate product obtained. With this in mind, the present process, when operated as a batch operation, is characterized by the use of vigorous mechanical stirring or shaking of the reactants and catalyst.

In continuous operations, in one embodiment, reactants can be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. As described herein, a portion of the catalyst can be continuously regenerated or reactivated by any suitable treatment and returned to the alkylation reactor.

This invention contemplates the resolution of problems associated with the regeneration of alkylation catalyst mixtures comprising a strong acid and methanesulfonic acid by the removal of at least a portion of the ASO contained within such mixtures. The accumulation of ASO in the alkylation catalysts occurs when an alkylation process continuously reuses its catalyst. In a continuous alkylation process, the ASO reaction by-product will build up in the catalyst until, if not removed, it reaches unacceptable concentration levels that can have negative effects upon the catalyst performance and, ultimately, the alkylation product quality. It is generally desirable to maintain the concentration of ASO in the alkylation catalyst at no more than about 20 weight percent of the catalyst with the weight percent ASO being based upon the total weight of the catalyst mixture exclusive of the ASO component. Preferably, the concentration of the ASO in the alkylation catalyst is less than about 15 weight percent, and most preferably, the concentration of ASO is less than 10 weight percent. There may be some process advantages in maintaining a low concentration of ASO in the catalyst mixture, but it is believed that an ASO concentration exceeding about 10 weight percent of the catalyst will have a detrimental effect upon the catalyst performance. Thus, in order to maintain the catalytic activity of the alkylation catalyst mixture, the catalyst must be processed to remove at least a portion of the ASO contained within such catalyst mixture.

This invention includes a process for removing ASO from a mixture containing a strong acid, methanesulfonic acid, and a concentration of ASO. Generally, the mixture is in the form of a single liquid phase which comprises, consists of or consists essentially of a strong acid component, a methanesulfonic acid component, and ASO.

The process includes a step wherein the mixture of a strong acid and methanesulfonic acid, having a concentration of ASO, is passed or introduced into separator means for separating at least a portion, preferably a major or substantial portion, of the strong acid component of the mixture therefrom. Separator means can be any apparatus which suitably provides for the separation of at least a portion, preferably a major portion, of the strong acid component of the mixture comprising a strong acid, methanesulfonic acid, and ASO so as to provide the two separate streams of a strong acid in vapor phase and a liquid phase. Such separation means can include, for example, distillation columns both of the tray type column and the packed type column, and flash vessels for performing a flash separation. The separation apparatuses define the separation zone into which the strong acid and methanesulfonic acid mixture is introduced.

The process conditions within the separation zone are generally maintained so as to induce the vaporization of at least a portion, preferably a major portion, of the strong acid contained in the strong acid and methanesulfonic acid mixture thereby producing a vapor stream, or an acid in vapor phase stream, comprising the vaporized strong acid. One problem associated with the use of separation techniques that use heat energy for providing the driving force for separating the strong acid component of the strong acid and methanesulfonic acid mixture is that the high temperatures required for the separation can result in undesirable decomposition of the methanesulfonic acid component of the mixture. Thus, to reduce the problems associated with the high temperature decomposition of methanesulfonic acid, it is advantageous for the process conditions within the separation zone to which the strong acid and methanesulfonic acid mixture is introduced to be maintained so as to minimize the amount of decomposition of the methanesulfonic acid component of the mixture.

Therefore, for best results, it is preferred for the separation of the strong acid from the mixture is to be a flash vaporization or separation wherein the separation zone is maintained at a pressure of less than about atmospheric pressure. Generally, the separation zone is operated at a pressure in the range of from about 0.1 to about 1 atmospheres of absolute pressure, preferably from about 0.5 to about 1 atmospheres of absolute pressure; and, most preferably, the separation zone is operated at a pressure in the range of from 0.75 to 1 atmospheres of absolute pressure. The operating temperature of the separation zone generally should be maintained so as to minimize the decomposition of the methanesulfonic acid component of the mixture and can be less than about 150° C., preferably, less than about 125° C.; and, most preferably, it can be maintained at less than 1000° C.

The inventive process also includes the step of mixing or contacting water with the liquid phase stream, which comprises methanesulfonic acid and ASO, to form a hydrous liquid phase stream. Any means or method can be used which suitably provides for the mixing or contacting of water with the liquid phase stream to produce the hydrous liquid phase stream. The hydrous liquid phase stream includes at least two intimately mixed, immiscible, liquid phases including, but not necessarily limited to, an ASO phase and a methanesulfonic acid with water phase. The immiscible liquid phases of the hydrous liquid phase stream can subsequently be separated into their respective phases. Any means or method can be used which suitably provides for the separating of the ASO phase from the methanesulfonic acid with water phase.

When mixing or contacting water with the liquid phase stream, any apparatus suitable for providing intimate mixing or contact can be used such as flow or line mixers and mechanically agitated vessels. Examples of flow or line type mixers include jet mixers, injectors, orifices, mixing nozzles, valves, pumps, agitated line mixers, packed tubes, pipe lines and the like. The mechanically agitated vessels include such devices as vessels equipped with propellers or impellers utilized to accomplish mixing and dispersion. It is generally desirable to use a continuous type process whereby the water is continuously mixed with the liquid phase stream followed by a separation of the resultant ASO phase and methanesulfonic acid with water phase by any means or method which suitably provides for separating the at least two immiscible liquid phases including the ASO phase and methanesulfonic acid with water phase. In the continuous process, it is common for the mixing or contacting step to be performed separately, and by a separate apparatus, from that of the separating step. Flow or line mixers provide suitable means for mixing in a continuous process. The mixing and separating steps can also be conducted in a batchwise fashion usually in a single vessel which defines both a mixing zone and a separation zone. Mechanically agitated vessels can be utilized as apparatus to permit the batchwise mixing of water and the liquid phase stream and separating of the resulting ASO and methanesulfonic acid with water phases. As for the separation of the immiscible liquid phases, a vessel, which defines a separation zone, can suitably be used; provided, it has the appropriate volume to permit the separation of the immiscible fluids by gravity or any other appropriate means. Other mechanical devices, such as, for example, centrifuges, can be used to perform the separation of the immiscible phases.

Any amount of water relative to the quantity of the liquid phase stream can be utilized in the process provided that the amount of water mixed with the liquid phase stream is sufficient for causing the subsequent formation of at least two immiscible, liquid phases including an ASO phase and a methanesulfonic acid with water phase. The ASO phase can comprise ASO, and the methanesulfonic acid with water phase can comprise water and at least a portion of the methanesulfonic acid component contained in the liquid phase stream. It is desirable to mix an amount of water with the liquid phase stream such that the volumetric ratio of the water component to the liquid phase stream exceeds about 0.25-to-1 to thereby form the hydrous liquid stream. Generally, the volumetric ratio of water to liquid phase stream in the hydrous liquid phase stream can be in the range of from about 0.5:1 to about 5:1. Preferably, the volumetric ratio of water to the liquid phase stream can be in the range of from about 1:1 to about 4:1; and, most preferably, it is between 2:1 to 3:1.

The ASO phase of the hydrous liquid phase stream can generally represent from about 1 to about 75 volume percent of the stream. But, preferably, the volume percent of the hydrous liquid phase stream constituting its ASO phase is in the range of from about 5 to about 50; and, most preferably, the volume percent can range from 10 to 30 of the hydrous liquid phase stream. The ASO phase, when allowed to separate from the methanesulfonic acid with water phase, will predominantly comprise ASO and can also include lesser fractional quantities of water and methanesulfonic acid. Generally, the volumetric percent of ASO in the ASO phase can be greater than about 80; but, preferably, the ASO will represent more than about 90 volume percent of the ASO phase. Most preferably, the ASO will constitute more than 95 volume percent of the ASO phase. Because it is impractical for the process to yield an ASO phase that is 100 percent ASO, the upper concentration limit of ASO in the ASO phase will approximate about 99 volume percent. Thus, the concentration range of ASO in the ASO phase will generally be in the range of from about 80 to about 99 volume percent, preferably from about 90 to about 99 volume percent, and most preferably from 95 to 99 volume percent.

The components which comprise the ASO phase, in addition to the ASO, can include water and methanesulfonic acid. The concentration of water in the ASO phase in most instances will be less than 15 volume percent and generally in the range of from about 0.01 to about 15 volume percent of the ASO phase. Preferably, the water concentration will be in the range of from about 0.1 to about 5 volume percent of the ASO phase; and, most preferably, it will be in the range of from 0.1 to 3 volume percent of the ASO phase. As for the methanesulfonic acid concentration of the ASO phase, in most instances, it will be less than about 15 volume percent, therefore, being in the range upwardly to about 15 volume percent. Preferably, the concentration of methanesulfonic acid in the ASO phase can range from about 0.5 to about 8 volume percent; and, most preferably, the methanesulfonic acid concentration in the ASO phase can range from 1 to 5 volume percent.

The methanesulfonic acid with water phase can comprise water and at least a portion of the methanesulfonic acid contained in the hydrous liquid phase stream. To have the most effective process, however, it is desirable for a major portion of the methanesulfonic acid component of the hydrous liquid phase stream to be recovered in the methanesulfonic acid with water phase; thus, in most instances, the fraction of the methanesulfonic acid contained in the hydrous liquid phase stream that can be recovered in the methanesulfonic acid with water phase can exceed about 50 volume percent. Preferably, the amount of methanesulfonic acid recovered can exceed about 60 volume percent; and, most preferably, the amount recovered will exceed 75 volume percent. While it is desirable to minimize the concentration of ASO in the methanesulfonic acid with water phase, in many instances, there can be a small concentration of ASO in the methanesulfonic acid with water phase. Generally, however, the concentration of ASO in the methanesulfonic acid with water phase can be less than about 20 volume percent, preferably, less than about 10 volume percent, and most preferably, less than 5 volume percent.

The process conditions under which the water and liquid phase stream can be mixed or contacted include mixing or contacting temperatures in the range of from about 0° F. to about 250° F., with 400° F. to 260° F. being preferred. The mixing or contacting pressures include those within the range of from about 0.5 atmospheres of absolute pressure to about 30 atmospheres of absolute pressure, with 0.95 atmospheres of absolute pressure to 25 atmospheres of absolute pressure being preferred. As for the process conditions under which the ASO phase and methanesulfonic acid with water phase are separated, the separating temperature can range from about 0° F. to about 250° F., with 40° F. to 260° F. being preferred. The separating pressures can range from about 0.5 atmospheres of absolute pressure to about 30 atmospheres of absolute pressure with preferred separating pressures being in the range of from 0.95 atmospheres of absolute pressure to 25 atmospheres of absolute pressure.

The methanesulfonic acid with water phase can further be processed to remove at least a portion of the water contained therein by any means suitable for removing or separating water from the methanesulfonic acid with water phase to thereby form a remaining portion of the methanesulfonic acid with water phase. For the best performance of the process, it is advantageous to remove a substantial portion of the water contained in the methanesulfonic acid with water phase to produce the remaining portion of methanesulfonic acid with water phase having a concentration of water of less than about 5 volume percent, but preferably, less than about 3 volume percent. Thus, the process step for separating at least a portion of the water contained in the methanesulfonic acid with water phase will produce two streams: a water stream having at least a portion, and preferably a significant portion, of the water contained in the methanesulfonic acid with water phase and the stream constituting the remaining portion of the methanesulfonic acid with water phase. The methanesulfonic acid with water phase, after having a portion of the water removed therefrom, or preferably, a significant portion of the water removed therefrom, can be utilized as at least a portion of an alkylation catalyst as earlier described herein.

Now referring to FIG. 1, there is depicted by schematic representation a process 10 which includes an alkylation reaction section 12 and a catalyst regeneration section 14. A hydrocarbon feed mixture, comprising olefins and isoparaffins, is introduced into riser-reactor 16 through conduit 18. Riser-reactor 16 defines a reaction zone wherein the hydrocarbon feed mixture is contacted, or admixed, with an alkylation catalyst, which comprises a strong acid and methanesulfonic acid, to thereby produce an alkylation reaction mixture comprising an alkylate product, ASO and the alkylation catalyst. The olefins of the hydrocarbon feed mixture generally comprise one or more olefins having from three to five carbon atoms, and the isoparaffins of the hydrocarbon feed mixture generally will have from four to six carbon atoms. The alkylation catalyst is introduced into riser-reactor 16 via conduit 20. The admixture of hydrocarbon feed mixture and alkylation catalyst passes through the reaction zone defined by riser-reactor 16 wherein a reaction takes place in which the olefins of the hydrocarbon feed mixture react with isoparaffins of the hydrocarbon feed mixture to produce the alkylate product. Also, within the reaction zone, the reaction by-product, ASO, is formed. The alkylation reaction mixture, or reaction effluent, from riser-reactor 16 passes to settler vessel 22, which defines a separation zone for separating the alkylate product from the alkylation reaction mixture to produce a separated reaction product 24 and a separated alkylation catalyst 26. Separated alkylation catalyst 26 will contain a substantial amount, or that amount that is riot soluble in the separated reaction product, of the alkylation reaction by-product, ASO. The separated alkylation catalyst 26 can be recycled via conduits 28 and 20 to riser-reactor 16 for reuse as the alkylation catalyst. Interposed in conduit 28 is catalyst cooler 30, which defines a heat transfer zone and provides means for exchanging heat from separated alkylation catalyst 26 to a heat transfer fluid such as water.

At least a portion, sometimes referred to as a slip stream or a drag stream, of the separated alkylation catalyst 26 passes by way of conduit 32 through heat exchanger 34 and control valve 36 and is introduced into separator vessel 38. Thus, the at least a portion of separated alkylation catalyst 26, or mixture comprising a strong acid, methanesulfonic acid and ASO, passes to separator vessel 38. Separator vessel 38 defines a separation zone and provides means for separating at least a portion of the strong acid component of the mixture therefrom to provide at least two separate streams one of which is an acid in vapor phase stream, comprising at least a portion of the strong acid component of the mixture, and the other being a liquid phase stream, comprising methanesulfonic acid and ASO. The separation zone defined by separator vessel 38 is maintained under such reduced pressure and temperature conditions as to permit the flash vaporization or separation of at least a portion of the strong acid contained in the mixture. Generally, the operating pressure of settler vessel 22 is greater than, and in many instances, substantially greater than, that of separator vessel 38. Preferably, in order to minimize the amount of decomposition of the methanesulfonic acid component of the mixture due to a high separation temperature, the separation zone defined by separator vessel 38 is maintained at a reduced pressure, which is preferably less than atmospheric. Thus, the mixture from settler vessel 22 passes through control valve 36 which throttles, or reduces, the pressure of the mixture stream as it enters separator vessel 38. Optionally, the mixture can be heated as it passes through heat exchanger 34 to separator vessel 38. As a result of the substantially adiabatic pressure drop across control valve 36, at least a portion of the mixture is flash vaporized to form the acid in vapor phase contained in vapor space 40 of separator vessel 38 with the remaining liquid phase 42 settling in the lower section of separator vessel 38. The acid in vapor phase stream passes by way of conduit 44 to compressor 46 which defines a compression zone and provides means for raising or increasing the pressure, or compressing, the acid in vapor phase stream to at least the pressure maintained in settler vessel 22. The compressed acid in vapor stream is discharged into conduit 48 and passes via conduit 48 to settler vessel 22 where it is recombined with separated alkylation catalyst 26. Interposed in conduit 48 is heat exchanger 50 which defines a heat transfer zone and provides means for condensing the compressed acid in vapor streams.

The liquid phase 42 stream from separator vessel 38 passes by way of conduit 52 to mixing means 54, which defines a mixing zone for mixing the liquid phase stream with water to thereby form a hydrous liquid phase stream which can subsequently form separate, immiscible ASO and methanesulfonic acid with water phases. Water is provided to the mixing zone defined by mixing means 52 through conduit 56. The resultant hydrous liquid phase stream then passes by way of conduit 58 to phase separator 60, which defines a separation zone for separating the hydrous liquid phase stream into an ASO phase 62, comprising ASO, and a methanesulfonic acid with water phase 64, comprising methanesulfonic acid and water. The ASO phase 62 passes to downstream processing via conduit 66, and the methanesulfonic acid with water phase 64 passes by way of conduit 68 to fractionator 70. Fractionator 70 defines a separation zone and provides means for separating at least a portion of the water contained in methanesulfonic acid with water phase 64 to form a remaining portion of the methanesulfonic acid with water phase 64. The separated water passes from fractionator 70 via conduit 72 to downstream processing. The remaining portion of the methanesulfonic acid with water phase passes from fractionator 70 by way of conduit 74 to settler vessel 22 wherein it is combined with the separated alkylation catalyst 26.

While this invention has been described in terms of the presently preferred embodiment, reasonable variations and modifications are possible by those skilled in the art. Such variations and modifications are within the scope of the described invention and the appended claims.

That which is claimed is:

1. A process for removing acid soluble oil (hereinafter "ASO") from a mixture containing methanesulfonic acid, ASO, and a strong acid selected from the group consisting of fluorosulfonic acid and trifluoromethanesulfonic acid, comprising the steps of:

passing said mixture to a separation zone, which is maintained at such conditions so as to induce the flash separation of at least a portion of the strong acid component of said mixture and to provide an acid in vapor phase stream and a liquid phase stream, wherein said acid in vapor phase stream comprises said at least a portion of the strong acid component of said mixture and wherein said liquid phase stream comprises methanesulfonic acid and ASO; and mixing water with said liquid phase stream to form a hydrous liquid phase stream wherein an amount of water is mixed with said liquid phase stream which is effective for causing the subsequent formation of an ASO phase and a methanesulfonic acid with water phase wherein said ASO phase comprises ASO and said methanesulfonic acid with water phase comprises methanesulfonic acid and water.

2. A process as recited in claim 1, wherein said amount of water mixed with said liquid phase stream is such that the volumetric ratio of the water to the liquid phase stream in said hydrous liquid phase stream is an amount exceeding about 0.25-to-1.

3. A process as recited in claim 2, further comprising the step of separating said hydrous liquid phase stream into said ASO phase and said methanesulfonic acid with water phase.

4. A process as recited in claim 3, wherein said ASO phase represents from about 1 to about 75 volume percent of said hydrous liquid phase stream.

5. A process a recited in claim 4, wherein an amount of water contained in said ASO phase is in the range of from about 0.01 to about 15 volume percent of said ASO phase.

6. A process as recited in claim 5, wherein the amount of methanesulfonic acid contained in said ASO phase is in the range upwardly to about 15 volume percent of said ASO phase.

7. A process as recited in claim 6, wherein an amount of ASO contained in said ASO phase is in the range of from about 80 volume percent to about 99 volume percent of said ASO phase.

8. A process as recited in claim 7, wherein the temperature of the mixing step is in the range of from about 0° F. to about 250° F., and the pressure of the mixing step is in the range of from about 0.5 atmospheres of absolute pressure to about 30 atmospheres of absolute pressure.

9. A process as recited in claim 8, wherein the temperature of the separating step is in the range of from about 0° F. to about 250° F. and the pressure of the separating step is in the range of from about 0.5 atmospheres of absolute pressure to about 30 atmospheres of absolute pressure.

10. A process as recited in claim 9, further comprising the step of separating at least a portion of the water contained in said methanesulfonic acid with water phase to additionally form a remaining portion of said methanesulfonic acid with water phase.

11. A process as recited in claim 10, further comprising the steps of:
utilizing said remaining portion of said methanesulfonic acid with water phase as at least a portion of an alkylation catalyst wherein said alkylation catalyst comprises a strong acid and methanesulfonic acid; and
contacting a hydrocarbon mixture, comprising olefins and isoparaffins, with said alkylation catalyst within a reaction zone to thereby produce an alkylation reaction mixture comprising an alkylate product, ASO, and said alkylation catalyst.

12. A process as recited in claim 11, further comprising the steps of:
separating said alkylate product from said alkylation reaction mixture within a first separation zone to produce a separated reaction product and a separated alkylation catalyst wherein said separated reaction product comprises at least a portion of said alkylate product and said separated alkylation catalyst comprises at least a portion of the ASO produced by said contacting step of claim 14; and
utilizing at least a portion of said separated alkylation catalyst as at least a portion of said alkylation catalyst.

13. A process as recited in claim 12, further comprising the step of optionally utilizing a remaining portion of said separated alkylation catalyst as said mixture.

14. A process as recited in claim 13, further comprising the step of utilizing said acid in vapor phase stream as at least a portion of said alkylation catalyst.

15. A process for separating acid soluble oil (hereinafter "ASO") from a mixture containing methanesulfonic acid, fluorosulfonic acid, and ASO, comprising the steps of:
passing said mixture to a separation zone which is maintained at a pressure and a temperature so as to vaporize at least a portion of the fluorosulfonic acid component of said mixture and to provide an acid in vapor phase stream and a liquid phase stream wherein said acid in vapor phase stream comprises fluorosulfonic acid and wherein said liquid phase stream comprises methanesulfonic acid and ASO;
contacting said liquid phase stream with water in an amount and under conditions suitable for forming an ASO phase and a methanesulfonic acid with water phase wherein said ASO phase comprises ASO and said methanesulfonic acid with water phase comprises methanesulfonic acid and water.

16. A process as recited in claim 15 wherein said pressure and said temperature of said separation zone is such so as to minimize the amount of decomposition of the methanesulfonic acid component of mixture.

17. A process as recited in claim 16 wherein the molar ratio of the fluorosulfonic acid component to methanesulfonic acid component of said mixture is in the range of from about 0.8 to about 2.0, and the ASO component of said mixture is present at a concentration of no more than about 20 weight percent of the mixture exclusive of the ASO component.

18. A process as recited in claim 17 wherein the ratio of volume of water to the volume of said liquid phase stream utilized in the contacting step exceeds about 0.25-to-1.

19. A process as recited in claim 18 wherein said at least a portion of the fluorosulfonic acid component of said mixture vaporized in said separation zone is a substantial portion of the fluorosulfonic acid component of said mixture.

20. A process as recited in claim 19 wherein:
the methanesulfonic acid component of said liquid phase stream is present in said liquid phase stream at a concentration of greater than about 80 percent; and
the ASO component of said liquid phase stream is present in said liquid phase stream at a concentration of less than about 20 percent.

21. A process as recited in claim 20 wherein the ASO component of said ASO phase is present in said ASO phase at a concentration exceeding about 60 percent.

22. A process as recited in claim 21 wherein the temperature of the contacting step is in the range of from about 0° F. to about 250° F., and the pressure of the contacting step is in the range of from about 0.5 atmospheres of absolute pressure to about 30 atmospheres of absolute pressure.

23. A process as recited in claim 22 wherein said pressure of said separation zone is less than about atmospheric pressure and said temperature of said separation zone is less than about 150° C.

24. A process for regenerating a mixture containing methanesulfonic acid, fluorosulfonic acid, and ASO, comprising the steps of:
  a) passing said mixture to a separation zone which is maintained at a reduced pressure so as to vaporize at least a portion of the fluorosulfonic acid component of said mixture to provide an acid in vapor phase stream and a liquid phase stream wherein said acid in vapor phase stream comprises fluorosulfonic acid and wherein said liquid phase stream comprises methanesulfonic acid and ASO;
  b) mixing water with said liquid phase stream to form a hydrous mixture wherein an amount of water mixed with said liquid phase stream is effective for causing the subsequent formation of an ASO phase and an methanesulfonic acid with water phase wherein said ASO phase comprises ASO and said methanesulfonic acid with water phase comprises water and at least a portion of the methanesulfonic acid component of said hydrous mixture;
  c) separating said methanesulfonic acid with water phase into a water stream and an acid stream wherein said water stream comprises water and wherein said acid stream comprises methanesulfonic acid;
  d) utilizing said acid stream as at least a portion of an alkylation catalyst comprising methanesulfonic acid and fluorosulfonic acid;
  e) contacting a hydrocarbon mixture, comprising olefins and isoparaffins, with said alkylation catalyst within a reaction zone to thereby produce an alkylation reaction mixture comprising said alkylation catalyst, an alkylate product, and ASO;
  f) separating said alkylate product from said alkylation reaction mixture within a separation zone to produce a separated reaction product and a separated alkylation catalyst wherein said separated reaction product comprises a portion of said alkylate product and said separated alkylation catalyst comprises a portion of the ASO produced by said contacting step (e);
  g) utilizing at least a portion of said separated alkylation catalyst as at least a portion of said alkylation catalyst;
  h) optionally utilizing a remaining portion of said separated alkylation catalyst as said mixture;
  i) compressing said acid in vapor phase stream; and
  j) passing the thus compressed acid in vapor stream to said separation zone.

* * * * *

UNITED STATES PATENT AND TRADEMARK OFFICE
CERTIFICATE OF CORRECTION

PATENT NO. : 5,284,993
DATED : February 8, 1994
INVENTOR(S) : Alan D. Eastman

It is certified that error appears in the above-identified patent and that said Letters Patent is hereby corrected as shown below:

Column 13, line 19, after "least" and before "portion", please delete "3" and insert therefor ---a---.

Signed and Sealed this

Eighteenth Day of October, 1994

Attest:

BRUCE LEHMAN

Attesting Officer

Commissioner of Patents and Trademarks